(12) United States Patent
Bonnstetter et al.

(10) Patent No.: US 9,060,702 B2
(45) Date of Patent: Jun. 23, 2015

(54) VALIDATION PROCESS FOR IPSATIVE ASSESSMENTS

(75) Inventors: Bill J. Bonnstetter, Scottsdale, AZ (US); Ronald J. Bonnstetter, Scottsdale, AZ (US); Dustin Hebets, Scottsdale, AZ (US); Thomas F. Collura, Chagrin Falls, OH (US)

(73) Assignee: Target Training International, Ltd., Scottsdale, AZ (US)

( * ) Notice: Subject to any disclaimer, the term of this patent is extended or adjusted under 35 U.S.C. 154(b) by 330 days.

(21) Appl. No.: 13/468,490

(22) Filed: May 10, 2012

(65) Prior Publication Data
US 2013/0303933 A1 Nov. 14, 2013

(51) Int. Cl.
| | |
|---|---|
| *A61B 5/04* | (2006.01) |
| *A61B 5/0476* | (2006.01) |
| *A61B 5/16* | (2006.01) |
| *G09B 7/02* | (2006.01) |
| *A61B 5/0484* | (2006.01) |

(52) U.S. Cl.
CPC ........... *A61B 5/0476* (2013.01); *A61B 5/04842* (2013.01); *A61B 5/04845* (2013.01); *A61B 5/164* (2013.01); *G09B 7/02* (2013.01)

(58) Field of Classification Search
USPC .................................................. 600/544, 545
See application file for complete search history.

(56) References Cited

U.S. PATENT DOCUMENTS

| | | | | |
|---|---|---|---|---|
| 5,170,780 | A | * | 12/1992 | Rosenfeld ...................... 600/544 |
| 5,551,880 | A | | 9/1996 | Bonnstetter et al. |
| 5,752,922 | A | | 5/1998 | Rosenfeld |
| 5,957,859 | A | | 9/1999 | Rosenfeld |
| 7,149,372 | B2 | | 12/2006 | Aoki et al. |
| 2004/0143170 | A1 | * | 7/2004 | DuRousseau ................. 600/300 |
| 2006/0183981 | A1 | | 8/2006 | Skinner |
| 2007/0191691 | A1 | | 8/2007 | Polanco |
| 2008/0177157 | A1 | * | 7/2008 | Pasricha et al. ............... 600/301 |
| 2008/0306811 | A1 | * | 12/2008 | Goldman et al. ............... 705/11 |

OTHER PUBLICATIONS

Davatzikos et al. Classifying spatial patterns of brain activity with machine learning methods: Application to lie detection. NeuroImage 28 (2005) 663-668.*
EP 13 15 8507—Target Training International Ltd.—European Search Report mailed Aug. 30, 2013.

\* cited by examiner

*Primary Examiner* — Etsub Berhanu
(74) *Attorney, Agent, or Firm* — McKee, Voorhees & Sease, PLC

(57) ABSTRACT

This invention is a validation process for ipsative assessments. Respondents are connected to an Electroencephalograph (EEG) and some or all of the ipsative assessment questions are asked again while connected to the EEG. The EEG measuring frontal lobe responses in terms of gamma waves is compared with the assessment questions. Positive responses provide one frontal lobe response in terms of gamma waves, negative or false answers provide a different gamma response and neutral questions provide a neutral gamma response. Reading the responses then tells whether the respondent initially responded with integrity, if so the assessment is validated.

8 Claims, 5 Drawing Sheets
(4 of 5 Drawing Sheet(s) Filed in Color)

Physical Health Assessment

Name _____ Age _____ Sex: ☐ Male ☐ Female

Do you primarily eat healthy foods? ☐ Yes ☐ No ☐ No Answer

Do you regularly exercise? ☐ Yes ☐ No ☐ No Answer

Are you happy with your current weight? ☐ Yes ☐ No ☐ No Answer

Do you think of yourself as a healthy person? ☐ Yes ☐ No ☐ No Answer

Instructions: Please select your preference for the items listed below. When you have completed the assessment, please review your answers and circle the the answer that you MOST like and LEAST like out of all of them.

1.) Dieting
☐ Hate ☐ Dislike ☐ Neutral ☐ Like ☐ Love

2.) Deep Fried Foods
☐ Hate ☐ Dislike ☐ Neutral ☐ Like ☐ Love

3.) Health Food
☐ Hate ☐ Dislike ☐ Neutral ☐ Like ☐ Love

4.) Calories
☐ Hate ☐ Dislike ☐ Neutral ☐ Like ☐ Love

5.) Exercise
☐ Hate ☐ Dislike ☐ Neutral ☐ Like ☐ Love

6.) Physically Fit
☐ Hate ☐ Dislike ☐ Neutral ☐ Like ☐ Love

7.) Overweight
☐ Hate ☐ Dislike ☐ Neutral ☐ Like ☐ Love

8.) Thin
☐ Hate ☐ Dislike ☐ Neutral ☐ Like ☐ Love

9.) Body Fat
☐ Hate ☐ Dislike ☐ Neutral ☐ Like ☐ Love

10.) Beer
☐ Hate ☐ Dislike ☐ Neutral ☐ Like ☐ Love

11.) Waist Size
☐ Hate ☐ Dislike ☐ Neutral ☐ Like ☐ Love

12.) Perfection
☐ Hate ☐ Dislike ☐ Neutral ☐ Like ☐ Love

13.) Sleep
☐ Hate ☐ Dislike ☐ Neutral ☐ Like ☐ Love

14.) Smoking
☐ Hate ☐ Dislike ☐ Neutral ☐ Like ☐ Love

15.) Walking
☐ Hate ☐ Dislike ☐ Neutral ☐ Like ☐ Love

16.) Running
☐ Hate ☐ Dislike ☐ Neutral ☐ Like ☐ Love

17.) Weight Lifting
☐ Hate ☐ Dislike ☐ Neutral ☐ Like ☐ Love

18.) Soda
☐ Hate ☐ Dislike ☐ Neutral ☐ Like ☐ Love

19.) Milk
☐ Hate ☐ Dislike ☐ Neutral ☐ Like ☐ Love

20.) Self Control
☐ Hate ☐ Dislike ☐ Neutral ☐ Like ☐ Love

21.) Wine
☐ Hate ☐ Dislike ☐ Neutral ☐ Like ☐ Love

22.) Chocolate Chip Cookies
☐ Hate ☐ Dislike ☐ Neutral ☐ Like ☐ Love

23.) Red Meat
☐ Hate ☐ Dislike ☐ Neutral ☐ Like ☐ Love

24.) Vegetables
☐ Hate ☐ Dislike ☐ Neutral ☐ Like ☐ Love

25.) Fresh Fruit
☐ Hate ☐ Dislike ☐ Neutral ☐ Like ☐ Love

26.) French Fries
☐ Hate ☐ Dislike ☐ Neutral ☐ Like ☐ Love

27.) Alcohol
☐ Hate ☐ Dislike ☐ Neutral ☐ Like ☐ Love

28.) Laziness
☐ Hate ☐ Dislike ☐ Neutral ☐ Like ☐ Love

29. Sugar
☐ Hate ☐ Dislike ☐ Neutral ☐ Like ☐ Love

30. Vitamins
☐ Hate ☐ Dislike ☐ Neutral ☐ Like ☐ Love

VALIDATION PROCESS FOR IPSATIVE ASSESSMENTS

FIELD OF THE INVENTION

The present invention relates to a method and system for validating ipsative assessments; and in particular, determining whether the respondent, who must make forced choices, has answered with integrity.

BACKGROUND OF THE INVENTION

Many assessments are available to predict or analyze the potential for success for a person at a particular job or task. Such assessments are different from right or wrong answer tests such as the Law School Aptitude Test (LSAT) or the Health School Entrance Exam (MCAT) or college entrance exams (ACT). That is to say, in forced answer assessments, the participant, often referred to herein as the respondent, must choose between several choices of varying degree. For example in one assessment depicted later in this Specification, as a physical health assessment requires the respondent to respond with respect to deep fried foods, i.e., whether they hate them, dislike them, are neutral towards them, like them, or love them. The answer has obvious health implications but depends upon the respondent's integrity. Heretofore, there have not been successful ways of validating ipsative assessment instruments to determine whether the person is giving true answers, answers they think are likely to be politically correct, or answers that they really believe. This one failing has made some potential customers for such assessments shy away from purchase of the instruments or from evaluating prospective employees by use of such assessments.

It has now been found that by using currently available electroencephalography science, one is able to develop a methodology for validating ipsative assessment instruments.

An electroencephalogram (EEG) measures and records the electroactivity of your brain. Special sensors (electrodes) are attached to one's head and hooked by wires to a computer. The computer records the brain's electrical activity on a screen or on a paper as wavy lines. EEG measures voltage fluctuations resulting form ionic current flows within the neurons of the brain. In clinical contexts, EEG refers to the recording of the brain's spontaneous electrical activity over a short period of time, as recorded from multiple electrodes placed on the scalp. Diagnostic applications generally focus on the spectral content of EEG, that is, the type of neural oscillations that can be observed in EEG signals. In neurology, the main diagnostic application of EEG is in the case of epilepsy, as epileptic activity can create clear abnormalities on a standard EEG study. A secondary clinical use of EEG is in the diagnosis of coma, encephalopathies, and brain death.

Heretofore, no one has used electroencephalography for combining with ipsative assessment taking to determine the integrity of the choices made by the respondents. This invention is premised upon such a discovery and the coupling of two widely different technologies.

It is therefore a primary objective of the present invention to provide a validation process for an ipsative assessment.

A further objective of the present invention is to provide a methodology for determining whether or not respondents, such as potential employees, are in fact answering assessment questions with integrity.

A further objective of the present invention is to provide enhanced value for ipsative assessments because one can rely with confidence on their results, knowing the respondents made truthful choices.

These, as well as other objectives and features of the present invention will be apparent from the following description and claims in conjunction with the accompanying drawings.

SUMMARY OF THE INVENTION

Ipsative assessments, that is, assessments that force answer choices for questions that are not simply the right-wrong answers, depend for their validation upon the integrity of the respondent. That is, the respondent must answer honestly so that the answers reflect their honest choices. This invention is a validation process for ipsative assessments. Respondents of the ipsative assessment are connected to an Electroencephalograph (EEG) and some or all of the ipsative assessment questions are asked again while connected to the EEG. The participant's EEG records, measuring frontal lobe responses in terms of gamma waves, are compared with the assessment questions. Positive responses provide one frontal lobe response in terms of gamma waves, negative or false answers provide a different gamma response and neutral questions provide a neutral gamma response. Reading the responses then tells whether the respondent initially responded with integrity, if so the assessment is validated.

BRIEF DESCRIPTION OF THE DRAWINGS

The patent or application file contains at least one drawing executed in color. Copies of this patent or patent application publication with color drawing(s) wil be provided by the Office upon request and payment of the necessary fee.

DETAILED DESCRIPTION OF THE PREFERRED EMBODIMENTS

Figure 1:
FIG. 1 shows a raw EEG with event markers.

This invention relates to ipsative assessments of the type shown for example in Bonnstetter U.S. Pat. Nos. 5,551,880 and 7,249,372, each of which are incorporated herein by reference.

With the result of this validation process for the first time, the soft science of personal assessment has been turned into a hard science by showing not just what people say is their self-reported ipsative response, but by validating their answers with corresponding brain activity. This unique approach exposes both qualitative and quantitative asymmetry of brain activity, thus exposing the underlying motivational system of decision making for the respondent or the participant.

The process of self-reporting by an individual, as a description of behaviors and beliefs, is a standard approach for many assessments. While these self-perception tools are commonly used and in many cases possess abundant statistical validation, including internal validity, correlation data and means comparisons, until now no process has linked these specific types of self-reports to actual brain activity. The new process uses asymmetric wave analysis resulting from a stimuli to validate the underlying mental decisions behind these self-reported responses, at the very moment of decision-making, thus exposing the true thoughts behind their responses and documenting potential abnormalities between their pre-assessments and their actual brain activity. This process provides evidence that an evoked emotionally laden response results in corresponding brain activity and documents both the intensity of human emotional response as well as the directionality of the response.

As described in Table 1, participants are first asked to respond to one of many self-reporting statistically validated assessment tools. These include ipsative surveys that address personal behaviors, motivators, mindsets, beliefs, and emotional intelligence, just to name a few. Once this data has been collected, selected individuals are asked to participate in the validation process. They first fill out a brief health report and review and sign consent forms before being directed to Applicants' Center for Applied Cognitive Research laboratory for phase II EEG data collection.

TABLE 1

Steps for Validating Ipsative Assessments

1. A participant first responds to the ipsative assessment and data is stored, both electronically and in the form of printed reports.
2. Participants are next exposed to matching ipsative items while connected to EEG.
3. Data from both forms of assessment are to be compared and contrasted for instrument validation.

There are many self-reporting statistical validated assessment tools that can be used with the process of this invention. For example, one may assess behaviors, motivators, beliefs, world view, emotional intelligence, and even health and prosperity issues with respect to such forced choice instruments.

Procedure/Examples

Once the EEG setup is complete, a verbal explanation of what to expect is provided and the sequence of events described. Participants are first shown a screen with their own EEG data flowing across the screen. They are made aware of the implications of various movements by having them blink their eyes, clinch their teeth, and move their head. After clarifying the need for reduced muscle movement, a baseline dataset is created by having one minute of recorded data with their eyes open and one minute closed. Finally, the programmed protocol begins with a brief screen prompted description of the task ahead. In each case, the task models as closely as possible the actual pre-assessed ipsative instrument assessment design.

Participants experience a series of stimuli allowing time to mentally form a semantic judgment concerning the personal descriptive nature of the stimuli. These stimuli may be in the form of words, phrases, images, video or sounds.

After artifact inspection, including eye blinks, each usable event is qualitatively and quantitatively assessed for stimulus power output and lobe asymmetry using several EEG wavelengths, including alpha (8-13 hz), beta (13-38 hz), and gamma (39-100 hz). (See FIG. 1 for an example of the raw EEG output with event markers.)

Referring to FIG. 1, the letter A represents the starting point of an event and is identifiable when the markers from channels 23 and 24 come together. Letter B indicates the point in the EEG when an online stimulus ends and is identifiable by the markers separating. The EEG area depicted on green represents one stimulus event.

To demonstrate the power of the process, a sample analysis of a physical health ipsative assessment will be used. As described in Table 1, each participant takes the survey and data is recorded. Below is a copy of the Physical Health Assessment, which is an example of ipsative assessment. Next, the participant is given the same instrument while connected to the EEG to determine the brain activity for each stimuli. An explanation of how to read these visual responses is provided in FIG. 2.

Figure 2A:
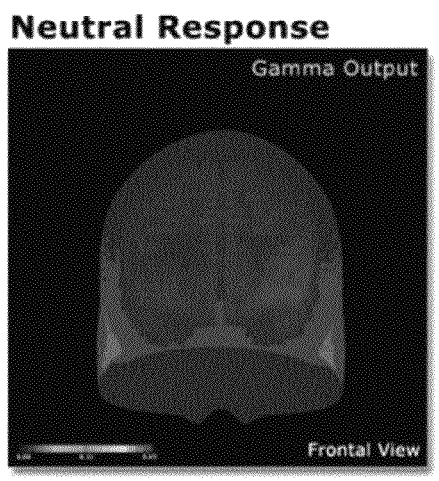
FIGS. 2A-2C shows neutral positive and avoidance responses with gamma wave output from an EEG, for example, of a respondent.
Figure 2B:
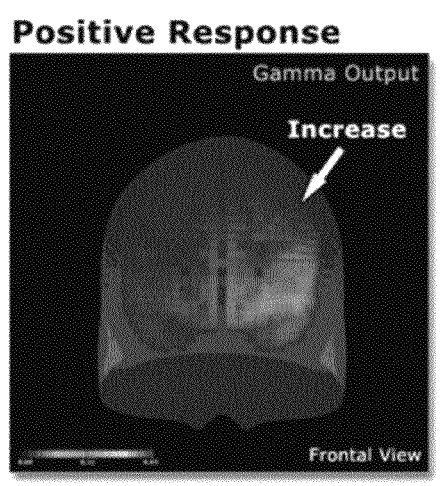
Figure 2C:
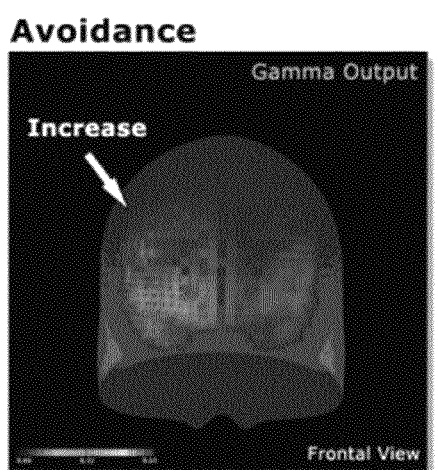

FIGS. 2A, 2B, and 2C show neutral positive and avoidance response in gamma output waves of the frontal lobes of a respondent. By way of explanation, a relative balance of gamma waves creating asymmetry in the activity in the frontal lobes is associated with normal mood and emotional state. Increased activity within the left prefrontal cortex can indicate an elevation in mood and positive feelings. De-activation in the left prefrontal cortex alone or in combination with an increase in activity within the right prefrontal cortex can suggest the opposite, being associated with depressive mood or negative thoughts. Instances in which only the right prefrontal cortex activates quickly with a strong increase in gamma waves suggest a strong dislike or avoidance of a particular exposure, sometimes called a negative response.

These example images of FIG. 2 depict the amount of gamma activity present in subjects' frontal lobes as they are exposed to different stimuli invoking neutral, positive, and negative responses.

Figure 3:
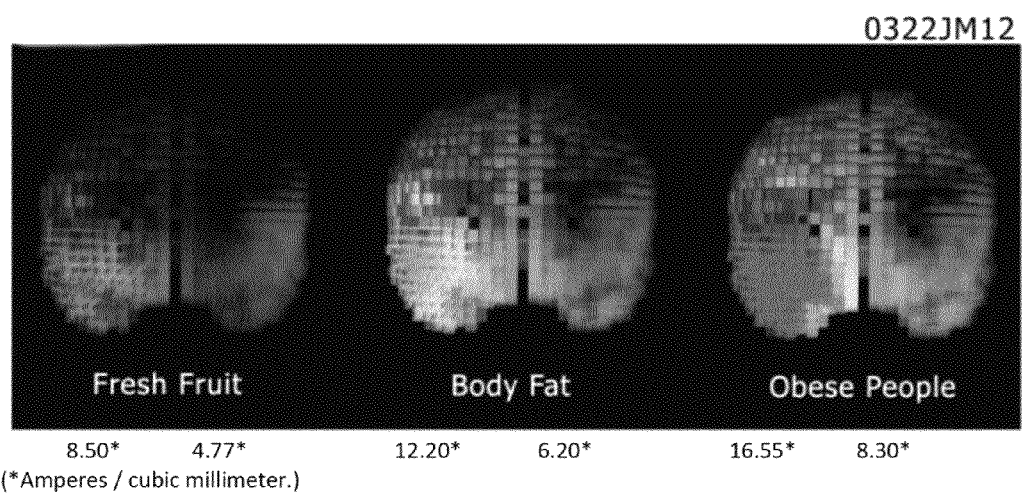
FIG. 3 shows actual prefrontal cortex gamma activity stimulus response to a person suffering from anorexia being exposed to the health assessment instrument shown later in the Specification.
Figure 4:
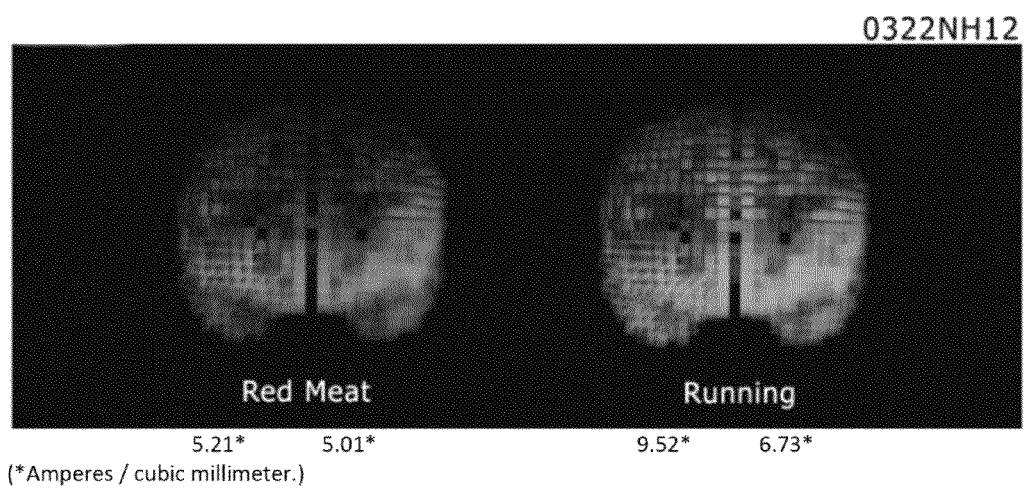
FIG. 4 shows another response to the same health assessment instrument for another particular patient.

In the case of the physical health assessment shown below, FIG. 3 shows an anorexic patient's prefrontal cortex for gamma activity stimulus response. In this sample, we see an extremely strong avoidance to the words "obese people" (increased activity in the right prefrontal cortex) and a similar but less intense reaction to "body fat". Even "fresh fruit" showed some negative reaction. In this example, the participant also responded to the survey with similar responses, thus showing a correlation between her ipsative survey and her brain activity, and in this case she therefore affirmed the accuracy of the original survey. FIG. 4 shows another participant's response to "red meat" and "running". In this case, we see a more positive response to "meat" and a strong, but neutral response to "running". These again affirm the pre-assessment data collected for this person.

With respect to the readout images shown in FIGS. 3 and 4, they relate to the physical health assessment shown in FIG. 5.

As one can see, in taking this assessment in FIG. 5, in order to have value it depends on the persons actually providing truthful answers. Using the validation system of the present invention assures those answers as given are truthful. For example, FIGS. 3 and 4 show two different respondent's answers, with FIG. 3 representing an individual who has fought anorexia most of her life, and FIG. 4 showing another participant's response to red meat and running. Since the individuals had both previously taken the full assessments, these answers with the EEG cap on affirm the pre-assessment data collected from the same individuals, and is validated.

It therefore can be seen that the invention accomplishes at least all of its stated objectives.

What is claimed is:

1. A method of validating ipsative assessment instrument responses comprising;

having a participant respond to an ipsative assessment instrument to provide participant first response data;

connecting said participant to an electroencephalograph (EEG);

having the participant again at least partially respond to the same ipsative assessment instrument while connected to the EEG to provide second response data and to provide EEG data measured in gamma activity while answering; and comparing the EEG data from the participant's frontal brain lobes with the participant's initial unconnected first response data to determine if the participant's first unconnected response data has integrity, and if so validating the participant's first response data.

2. The method of claim 1 wherein the ipsative instrument is selected from the group consisting of behaviors, motivators, world view, emotional intelligence, beliefs and health and prosperity forced choice instruments.

3. The method of claim 1 wherein a response that has integrity is determined by asymmetric wave analysis.

4. A method of determining whether responses to an ipsative assessment instrument are valid, comprising:
   receiving a first set of responses from a participant to an ipsative assessment instrument, wherein the first set of responses includes a first response to a first portion of the ipsative assessment instrument;
   connecting the participant to an electroencephalograph machine (EEG machine);
   after receiving the first set of responses, exposing the participant to a stimulus that corresponds with the first portion of the ipsative assessment instrument while the participant is connected to the EEG machine;
   measuring gamma wave electrical activity of a frontal brain lobe of the participant using the EEG machine while the participant is being exposed to the stimulus;
   creating an image of the participant's gamma brain waves based on the measured electrical activity of the frontal brain lobe of the participant;
   inspecting the image of the participant's gamma brain waves to determine whether the electrical activity in the participant's frontal lobe while the participant is being exposed to the stimulus is consistent with the first response; and
   validating the first set of responses if the electrical activity in the participant's frontal lobe is consistent with the first response.

5. The method of claim 4, wherein the ipsative instrument comprises a plurality of ipsative questions and the first portion comprises at least one, but less than all, of the plurality of ipsative questions.

6. The method of claim 5, wherein the stimulus comprises showing the participant the first portion of the ipsative assessment.

7. The method of claim 5, wherein the stimulus comprises showing the participant an image that relates to the first portion of the ipsative assessment.

8. The method of claim 4, wherein the image of the participant's brain waves is determined to be consistent with the first response based upon asymmetric brain wave patterns across left and right sides of the participant's brain.

* * * * *